United States Patent
Yamaoka et al.

(10) Patent No.: US 11,253,626 B2
(45) Date of Patent: Feb. 22, 2022

(54) USE FOR PEPTIDE UNIQUELY BINDING TO VASCULAR ENDOTHELIAL CELLS, AND PEPTIDE

(71) Applicants: NATIONAL CEREBRAL AND CARDIOVASCULAR CENTER, Osaka (JP); JMS CO., LTD., Hiroshima (JP)

(72) Inventors: Tetsuji Yamaoka, Osaka (JP); Maria Chiara Munisso, Osaka (JP); Atsushi Mahara, Osaka (JP); Takashi Yamamoto, Hiroshima (JP)

(73) Assignees: NATIONAL CEREBRAL AND CARDIOVASCULAR CENTER, Osaka (JP); JMS CO., LTD., Hiroshima (JP)

( * ) Notice: Subject to any disclaimer, the term of this patent is extended or adjusted under 35 U.S.C. 154(b) by 0 days.

(21) Appl. No.: 16/481,662

(22) PCT Filed: Jan. 30, 2018

(86) PCT No.: PCT/JP2018/002886
§ 371 (c)(1),
(2) Date: Jul. 29, 2019

(87) PCT Pub. No.: WO2018/139665
PCT Pub. Date: Aug. 2, 2018

(65) Prior Publication Data
US 2019/0365944 A1 Dec. 5, 2019

(30) Foreign Application Priority Data
Jan. 30, 2017 (JP) .............................. JP2017-014800

(51) Int. Cl.
| | | |
|---|---|---|
| *A61L 17/14* | (2006.01) | |
| *A61L 17/10* | (2006.01) | |
| *A61L 27/16* | (2006.01) | |
| *A61L 27/28* | (2006.01) | |
| *A61L 27/50* | (2006.01) | |
| *A61L 31/04* | (2006.01) | |
| *A61L 31/08* | (2006.01) | |
| *A61L 33/12* | (2006.01) | |

(52) U.S. Cl.
CPC ............ *A61L 17/145* (2013.01); *A61L 17/10* (2013.01); *A61L 27/16* (2013.01); *A61L 27/28* (2013.01); *A61L 27/507* (2013.01); *A61L 31/043* (2013.01); *A61L 31/08* (2013.01); *A61L 33/12* (2013.01); *A61L 2300/25* (2013.01)

(58) Field of Classification Search
None
See application file for complete search history.

(56) References Cited

U.S. PATENT DOCUMENTS

| | | | |
|---|---|---|---|
| 2002/0048763 A1 | 4/2002 | Penn et al. | |
| 2002/0102252 A1 | 8/2002 | Gu et al. | |
| 2004/0063134 A1 | 4/2004 | Gu et al. | |
| 2007/0271630 A1* | 11/2007 | Boukharov | ........ C12N 15/8241 800/279 |
| 2008/0057097 A1 | 3/2008 | Benco et al. | |
| 2015/0272719 A1 | 10/2015 | Yamaoka et al. | |
| 2017/0158737 A1* | 6/2017 | Chuang | .............. C12N 15/1037 |
| 2017/0240596 A1 | 8/2017 | Cheng et al. | |

FOREIGN PATENT DOCUMENTS

| | | |
|---|---|---|
| CN | 104592352 | 5/2015 |
| CN | 106518968 | 3/2017 |
| JP | 2010-502363 | 1/2010 |
| WO | 01/57272 | 8/2001 |
| WO | 01/57273 | 8/2001 |
| WO | 01/57274 | 8/2001 |
| WO | 01/57275 | 8/2001 |
| WO | 01/57276 | 8/2001 |
| WO | 01/57277 | 8/2001 |
| WO | 01/57278 | 8/2001 |

(Continued)

OTHER PUBLICATIONS

Wang et al., "Rapid Detection of Pathogenic Bacteria and Screening of Phage-Derived Peptides Using Microcantilevers", Analytical Chemistry, 2014, pp. 1671-1678, vol. 86, No. 3.

(Continued)

*Primary Examiner* — Maury A Audet
(74) *Attorney, Agent, or Firm* — Greenblum & Bernstein, P.L.C.

(57) ABSTRACT

Provided is a use for a peptide in surface-treating a medical device or medical material to be used in contact with blood, with which it is possible to obtain a medical device or medical material that can achieve highly efficient vascular endothelialization through the use of a peptide uniquely binding to vascular endothelial cells. Also provided are: a peptide suitable for use in said surface treatment; a method for producing a medical device or medical material surfaced-treated with said peptide and to be used in contact with blood; and a surface treatment agent including said peptide, said agent to be used in surface-treating a medical device or medical material to be used in contact with blood. In the present invention, a medical device or medical material is surface-treated using a peptide that includes any one of ten specific amino acid sequences and uniquely binds to the surface of endothelial progenitor cells.

4 Claims, No Drawings
Specification includes a Sequence Listing.

(56) References Cited

FOREIGN PATENT DOCUMENTS

| WO | 01/86003 | 11/2001 |
| WO | 2008/030388 | 3/2008 |
| WO | 2013/125221 | 8/2013 |
| WO | 2014/065017 | 5/2014 |
| WO | 2016/172722 | 10/2016 |

OTHER PUBLICATIONS

International Search Report issued in International Patent Application No. PCT/JP2018/002886, dated May 1, 2018 with English Translation.
International Preliminary Report on Patentability issued with respect to Patent Application No. PCT/JP2018/002886, dated Jul. 30, 2019 with English translation.

* cited by examiner

SEQUENCE LISTING

```
<160> NUMBER OF SEQ ID NOS: 20

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Gly Gln Ser Glu Lys His Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

His Gly Gly Val Arg Leu Tyr
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Ser Phe Lys Ile Pro Tyr His Tyr Asp Ser Gly Gln
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Ser Leu Ser Lys Trp Ser Phe
```

```
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Lys Ile Ala Val Ile Ser Thr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Thr Asp Asn Thr Lys Pro Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Thr Asn Trp Arg Thr Ile Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 8

Val Ser Arg Asp Thr Pro Gln
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 9

Thr Ile Pro Arg Ala Pro Ser Pro Ala Asn Thr Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 10

Asn Arg Pro Asp Ser Ala Gln Phe Trp Leu His His
1               5                   10
```

```
<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 11

Gly Gln Ser Glu Lys His Leu Gly Gly Gly Cys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 12

His Gly Gly Val Arg Leu Tyr Gly Gly Gly Cys
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 13

Ser Phe Lys Ile Pro Tyr His Tyr Asp Ser Gly Gln Gly Gly Gly Cys
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 14

Ser Leu Ser Lys Trp Ser Phe Gly Gly Gly Cys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 15

Lys Ile Ala Val Ile Ser Thr Gly Gly Gly Cys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 16

Thr Asp Asn Thr Lys Pro Lys Gly Gly Gly Cys
1               5                   10
```

```
<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 17

Thr Asn Trp Arg Thr Ile Asn Gly Gly Gly Cys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 18

Val Ser Arg Asp Thr Pro Gln Gly Gly Gly Cys
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 19

Thr Ile Pro Arg Ala Pro Ser Pro Ala Asn Thr Tyr Gly Gly Gly Cys
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 20

Asn Arg Pro Asp Ser Ala Gln Phe Trp Leu His His Gly Gly Gly Cys
1               5                   10                  15
```

USE FOR PEPTIDE UNIQUELY BINDING TO VASCULAR ENDOTHELIAL CELLS, AND PEPTIDE

TECHNICAL FIELD

The present invention relates to a use of a peptide specifically binding to vascular endothelial cells in surface treatment of a medical device or medical material to be used in contact with blood; a peptide suitable for use in the surface treatment; a production method of a medical device or medical material surface-treated with the peptide and to be used in contact with blood; and a surface treatment agent including the peptide for surface-treating a medical device or medical material to be used in contact with blood.

BACKGROUND ART

Conventionally, for implanted medical devices such as artificial blood vessels, artificial valves, and stents used in contact with blood, improvement in antithrombogenicity or biocompatibility has been desired. For example, attempts have been made to improve the antithrombogenicity on surfaces of various materials by immobilizing vascular endothelial cell-binding protein or peptide on a surface of an implanted medical device.

Specifically, a method for suppressing formation of a thrombus by using a biologically derived extracellular matrix as a material for an artificial blood vessel, and immobilizing a vascular endothelial cell-adhesive peptide having a specific sequence including an REDV sequence on a lumen of the artificial blood vessel has been proposed (Patent Document 1). Furthermore, there has been proposed a method for promoting endothelialization of a surface of a medical device such as a vascular stent by coating with a peptide including an RGD sequence or a YIGSR sequence derived from a binding domain of cell adhesion proteins such as fibronectin, vitronectin, laminin, elastin, fibrinogen, and collagen after the medical device is placed in the blood vessel (Patent Document 2).

Patent Document 1: PCT International Publication No. WO2014/065017

Patent Document 2: Japanese Unexamined Patent Application (Translation of PCT Application), Publication. No. 2010-502363

DISCLOSURE OF THE INVENTION

Problems to be Solved by the Invention

In the sequences used in Patent Documents 1 and 2, the REDV sequence and the RGD sequence are cell adhesion peptide sequences found from fibronectin as a representative cell adhesion molecule, and the YIGSR sequence is a cell adhesion peptide sequence found from laminin as a cell adhesion molecule. Therefore, the REDV sequence, the RGD sequence, the YIGSR sequence, and the like, have affinity to various adhesive cells, and do not necessarily have high selectivity with respect to the vascular endothelial cells. Therefore, a surface treatment method capable of achieving high efficiency of endothelialization on a surface of a medical device or medical material to be used in contact with blood has been demanded.

The present invention has an object to provide a use of a peptide in surface treatment of a medical device or medical material to be used in contact with blood, the surface treatment being capable of obtaining a medical device or medical material that can achieve high efficiency of endothelialization by use of a peptide specifically binding to vascular endothelial cells; a peptide suitably used in the above-described surface treatment; a production method of a medical device or medical material surface-treated with the above-described peptide and to be used in contact with blood; and a surface treatment agent including the above-described peptide for surface-treating a medical device or medical material to be used in contact with blood.

Means for Solving the Problems

The present inventors have found that the above-mentioned problems can be solved by using a peptide including any one of ten specific types of amino acid sequences specifically binding to a surface of a vascular endothelial progenitor cell, and by performing surface treatment of a medical device or medical material, and the present inventors have completed the present invention.

Effects of the Invention

The present invention can provide a use of a peptide in surface treatment of a medical device or medical material to be used in contact with blood, the surface treatment being capable of obtaining a medical device or medical material that can achieve high efficiency of endothelialization by use of a peptide specifically binding to vascular endothelial cells; a peptide suitably used in the above-described surface treatment; a production method of a medical device or medical material surface-treated with the above-described peptide and to be used in contact with blood; and a surface treatment agent including the above-described peptide for surface-treating a medical device or medical material to be used in contact with blood.

PREFERRED MODE FOR CARRYING OUT THE INVENTION

First Embodiment

A first embodiment of the present invention relates to a use of a peptide in surface treatment of a medical device or medical material to be used in contact with blood, the peptide including an amino acid sequence of any one of SEQ ID NOs: 1 to 10. Note here that in the specification and claims of the present application, the term "peptide" without any special description means a peptide including an amino acid sequence of any one of SEQ ID NOs: 1 to 10.

The amino acid sequences of SEQ ID NOs: 1 to 10 are as follows.

```
                            (SEQ ID NO: 1)
GQSEKHL (SEQ ID NO: 2)
HGGVRLY (SEQ ID NO: 3)
SFKIPYHYDSGQ (SEQ ID NO: 4)
SLSKWSF (SEQ ID NO: 5)
KIAVIST
```

-continued

TDNTKPK (SEQ ID NO: 6)

TNWRTIN (SEQ ID NO: 7)

VSRDTPQ (SEQ ID NO: 8)

TIPRAPSPANTY (SEQ ID NO: 9)

NRPDSAQFWLHH (SEQ ID NO: 10)

The peptide having an amino acid sequence of any one of SEQ ID NOs: 1 to 10 specifically binds to a vascular endothelial progenitor cell (EPC) or blood circulating cells having a similar property, but does not easily bind to platelets that cause the formation of a thrombus. Therefore, a peptide having an amino acid sequence including any one of the SEQ ID NOs: 1 to 10 also specifically binds to a vascular endothelial progenitor cell or blood circulating cells having a similar property, but does not easily bind to platelets that cause the formation of a thrombus. Hereinafter, a site having an amino acid sequence including any one of the SEQ ID NOs: 1 to 10 in the peptide is also referred to as an "EPC binding site".

Hereinafter, the first embodiment will be described in detail.

<Medical Device or Medical Material>

Surface treatment of a medical device or medical material is performed using the above-described specific peptide. As the medical device or the medical material, a device or material to be used in contact with blood is used. By surface-treating a medical device or medical material to be used in contact with blood using a peptide described below, it is possible to obtain a medical device or medical material capable of achieving high efficiency of endothelialization. The medical device or the medical material is not particularly limited as long as it includes a site that is brought into contact with blood at the time of use.

Suitable examples of the medical device include one or more selected from the group consisting of an artificial blood vessel, a stent, an artificial valve, a catheter, a balloon, an artificial heart pump, and an artificial lung. Examples of the medical device including two or more medical devices in combination include an artificial blood vessel having an artificial valve, a stent graft that is an artificial blood vessel (graft) having a stent, and the like.

The material of a surface-treated portion in these medical devices is not particularly limited, and a material conventionally used in general in the medical devices may be employed.

Suitable specific examples of the medical materials include one selected from the group consisting of a fiber, a film, a sheet, a bag, a tube, a woven fabric, a nonwoven fabric, a molded product, and a biologically derived tissue, as well as a composite material including two or more of these materials.

These materials constituting a surface to be surface-treated in the medical device or the medical material may be an organic material or an inorganic material, and may be a composite such as a resin, and may be natural products derived from animals or plants. Furthermore, these materials may be materials obtained by chemically denaturing or modifying natural products.

Specific examples of the material constituting a surface to be surface-treated in the medical device or the medical material include natural polymers such as collagen, gelatin, fibrin, alginic acid, cellulose and chitin; polyglycolic acid (PGA), polylactic acid (PLA), polycaprolactone (PCL), polyethylene glycol (PEG), polymethylene carbonate, polydioxanone, and copolymers thereof; synthetic resins such as polyethylene, polypropylene, polyamides, polyesters (polyethylene terephthalate, etc.), polycarbonates, fluorocarbon resins, polyurethanes, polystyrene, polyacrylonitrile, polyvinyl alcohol, polyvinyl chloride, polymethyl methacrylate, and polydimethylsiloxane; ceramics such as alumina, zirconia, and apatite; metal materials such as stainless steel, cobalt alloys, titanium, and titanium alloys; and inorganic materials such as calcium carbonate and calcium phosphate.

For the medical material, fibers, or fibers constituting the woven fabric or nonwoven fabric may be twine or non-twine, and may be a monofilament or a multifilament. Furthermore, a film, a sheet, a bag, a tube, and other various molded products may be formed of a porous material or a laminated material.

The biologically derived tissue includes tissues such as those of the cornea, heart valve, blood vessel, skin, cartilage, bone, tendon, muscle, bladder, small intestine, heart, liver, lung, trachea, esophagus, lens, vitreous body, retina, nerve, adipose tissue, brain, dura mater, pleura, diaphragm, ureter, kidney, pancreas, gallbladder, gingiva, periodontal membrane, teeth, placenta, and reproductive organs.

Among the biologically derived tissues, from the viewpoint that the amount of contact with blood is large, and the like, a heart valve, a blood vessel, a heart, and the like, are preferable, and the blood vessel is more preferable. These biologically derived tissues are usually used in a state formed of an extracellular matrix which is decellularized and which does not include cells. The method for decellularizing biologically derived tissues is not particularly limited, and decellularizing is performed according to a well-known method. For example, an artificial blood vessel prepared by using such an extracellular matrix can be basically an artificial blood vessel having high biocompatibility and low rejection.

A living body as a supply source of the biologically derived tissue is not particularly limited, and can be, for example, a non-human animal (e.g., a ratite, a bird, a mammal, or the like). The mammal is not particularly limited, and examples thereof include a rabbit, a goat, a sheep, a pig, a horse, a cow, a monkey, or the like. The ratite is not particularly limited, but examples thereof include an emu, a kiwi, an ostrich, a cassowary, a rhea, or the like. In general, a ratite has a long neck, and blood vessels such as the carotid artery that is present in the neck are thin and long and hardly have a bifurcation. For this reason, by producing an artificial blood vessel with the use of a blood vessel of ratites, it is possible to provide an artificial blood vessel whose lumen has a smaller cross section and which is longer and has fewer bifurcations. Such an artificial blood vessel is very useful in the clinical field. Furthermore, ratites and the like are easy to raise, and it is therefore possible to stably supply a large volume of vascular tissue.

From the viewpoint of ease in processing into various shapes, no or little undesirable effect on a living body or blood, stability in a living body, and the like, the material of the surface of the medical device or the medical material is also preferably, for example, a fluorocarbon resin.

Examples of the fluorocarbon resin include PTFE (polytetrafluoroethylene resin), PFA (copolymer of tetrafluoroethylene and 1-perfluoroalkoxy-1,2,2-trifluoroethylene), FEP (copolymer of tetrafluoroethylene and hexafluoropropylene), ETFE (copolymer of tetrafluoroethylene and ethylene), PCTFE (polychlorotrifluoroethylene resin), PVdF (polyvinylidene fluoride resin), and the like. Among these fluorocarbon resins, from the viewpoint of workability, chemical stability, and the like, PTFE (polytetrafluoroethylene resin) is preferable.

<Peptide>

The peptide to be used in the surface treatment of the above-mentioned medical device or medical material has an amino acid sequence of any one of SEQ ID NOs: 1 to 10 in the sequence of the peptide as described above. The peptide having such a sequence specifically binds to a vascular endothelial progenitor cell but does not easily bind to platelets that cause the formation of a thrombus. Therefore, on the surface of the medical device or the medical material surface-treated with the peptide, the generation of a thrombus is suppressed, and high efficiency of vascular endothelialization can be easily achieved.

A position of the amino acid sequence of any one of SEQ ID NOs: 1 to 10 in the peptide sequence is not particularly limited within a range where the objects of the present invention are not impaired. From the viewpoint that steric hindrance is small, and a human vascular endothelial progenitor cell and a peptide easily bind to each other satisfactorily, it is preferable that in the peptide sequence, the amino acid sequence of any one of SEQ ID NOs: 1 to 10 is present in the vicinity of the non-binding terminal that is a terminal distant from the binding site between the surface of the medical device or the medical material and the peptide. The non-binding terminal may be the C-terminal or the N-terminal of the peptide.

Specifically, the number of amino acid residues that are present between the non-binding terminal of the peptide and the terminal at the non-binding terminal side of a site having an amino acid sequence of any one of SEQ ID NOs: 1 to 10 is an integer of preferably 0 or more and 5 or less, and more preferably 0.

The full length of the peptide is not particularly limited as long as a desired effect by surface treatment can be obtained. The full length of the peptide is preferably 80 amino acid residues or less, more preferably 50 amino acid residues or less, further preferably 30 amino acid residues or less, further more preferably 20 amino acid residues or less, and particularly preferably 15 amino acid residues or less. Furthermore, from the viewpoint that the preparation of a peptide is easy, and a desired surface treatment effect can be easily obtained, a peptide sequence which does not include sequences other than the sequence of SEQ ID Nos: 1 to 10 is preferable. In other words, the peptide may be a peptide having an amino acid sequence of any one of SEQ ID NOs: 1 to 10.

The peptide may include an adhesion site having adhesiveness with respect to the surface of the medical device or the medical material. When the peptide includes such an adhesion site, by bringing the peptide into contact with a surface of the medical device or the medical material, the peptide can be easily supported on the surface of the medical device or the medical material.

Examples of the adhesion site include an adhesion site including amino acid residues having a 2,3-dihydroxyphenyl group or a 3,4-dihydroxyphenyl group. Since the adhesion site including amino acid residues having a 2,3-dihydroxyphenyl group or a 3,4-dihydroxyphenyl group has a dihydroxyphenyl group in which two hydroxyl groups are adjacent, the adhesion site can bind to a surface of the medical device or the medical material. When the medical device or the medical material is made of a metal material, the peptide binds to the surface via the adhesion site by the chelation of a metal atom that is present on the surface and a dihydroxyphenyl group. When the medical device or the medical material is made of a material such as an organic polymer having a functional group including active hydrogen such as a hydroxyl group and an amino group, or a ceramic, quinone generated by oxidation of the dihydroxyphenyl group and a functional group including active hydrogen such as a hydroxyl group or an amino group react with each other, so that an adhesive peptide binds to the surface of the medical device or the medical material via the adhesion site.

Out of the 2,3-dihydroxyphenyl group and the 3,4-dihydroxyphenyl group, from the viewpoint of ease in reaction with a surface of the medical device or the medical material, the 3,4-dihydroxyphenyl group is preferable. Specific examples of the amino acid including the 3,4-dihydroxyphenyl group include 3-(3,4-dihydroxyphenyl)-L-alanine (L-DOPA), 3-(3,4-dihydroxyphenyl)-2-methyl-L-alanine (methyl DOPA), (3R)-3-(3,4-dihydroxyphenyl)-L-serine (DOPS), and the like. Among them, from the viewpoint of ease in availability when the peptide is actually prepared, and the like, 3-(3,4-dihydroxyphenyl)-L-alanine (L-DOPA) is preferable.

An adhesion site made of amino acid residues having a 2,3-dihydroxyphenyl group or a 3,4-dihydroxyphenyl group is present within preferably 10 amino acid residues and more preferably 5 amino acid residues from the terminal opposite to the non-binding terminal of the peptide.

Furthermore, when the surface of the medical device or the medical material is made of the above-described biologically derived tissue, the adhesion site is also preferably a site having a repetitive sequence of an amino acid represented by (POG)n. Herein, P represents proline, O represents hydroxyproline, G represents glycine, and n represents the number of repetitions of the amino acid sequence in the parentheses. The number of n is not particularly limited, but the number may be an integer of 1 or more and 20 or less, an integer of 2 or more and 20 or less, an integer of 3 or more and 20 or less, an integer of 4 or more and 20 or less, an integer of 5 or more and 20 or less, an integer of 6 or more and 20 or less, an integer of 7 or more and 20 or less, an integer of 8 or more and 20 or less, an integer of 9 or more and 20 or less, and an integer of 10 or more and 20 or less.

The adhesion site having the repetitive sequence of the amino acid represented by (POG)n is preferably present in the vicinity of the terminal opposite to the non-binding terminal in the peptide. Specifically, the number of amino acid residues present between the terminal opposite to the non-binding terminal in the peptide and the terminal near the terminal opposite to the non-binding terminal in the peptide in the site having a repetitive sequence of the amino acid represented by (POG)n is preferably an integer of 0 or more 5 or less, and more preferably 0.

When the peptide has the above-mentioned adhesion site, the peptide may include a spacer site having an arbitrary amino acid sequence between the adhesion site and a site having an amino acid sequence of any one of SEQ ID NOs: 1 to 10. It is preferable that the amino acid sequence of the spacer site includes many amino acid residues such as glycine and alanine which do not have a side chain having a large size and high polarity because the influence on the three-dimensional structure of the site having the amino acid sequence of SEQ ID NOs: 1 to 10 is small.

The above-described peptide can be obtained by a well-known technique according to the designed amino acid sequence. Examples of suitable methods include a solid-phase synthesis method such as an Fmoc method or a Boc method. Crude peptides obtained by such a solid phase synthesis method can be purified using a method such as reverse-phase HPLC if necessary. Whether or not the obtained peptide has a desired sequence can be determined by well-known means. Such means include a method of comparing a molecular weight of a peptide measured by MALDI-TOF/MS with a theoretical molecular weight of the peptide calculated by the amino acid sequence.

<Surface Treatment Method>

The surface treatment of a medical device or medical material is not particularly limited as long as it is a method that can cause a peptide to be supported on a surface of the medical device or the medical material. Typically, surface treatment with a peptide can be performed by causing a peptide to bind or attach to a surface of the medical device or the medical material.

The peptide on the surface of the medical device or the medical material may be supported by, for example, a weak bond through interaction between molecules, or may be supported by forming a covalent bond between the surface and the peptide. The method for forming a covalent bond between the surface and the peptide is not particularly united. Typical methods include a method of condensing the reactive functional groups such as a hydroxyl group, a carboxy group, and an amino group which are present on the surface with functional groups such as a carboxy group, an amino group, and a hydroxyl group which are present in the peptide. When the peptide is caused to bind to the surface by condensation, it is preferable that the surface and the peptide are condensed by using a well-known condensing agent. The type of the condensing agent is not particularly limited as long as the condensing agent does not adversely affect the peptide and the medical device or the medical material, and can be appropriately selected depending on the types of the functional groups relating to the condensation reaction. Furthermore, the surface to be surface-treated in the medical device or the medical material may not be specially subjected to pre-treatment or may be subjected to pre-treatment.

The peptide may be directly supported on the surface of the medical device or the medical material. Furthermore, a linker site may be formed by causing a linker compound to be supported on a surface of the medical device or the medical material, and then the peptide may be supported on the surface of the medical device or the medical material via a linker site.

The peptide is supported on the surface of the medical device or the medical material by bringing the surface of the medical device or the medical material into contact with the peptide. The method of bringing the surface of the medical device or the medical material into contact with the peptide is not particularly limited. When the surface of the medical device or the medical material is brought into contact with the peptide, since the medical device or the medical material is easily brought into uniform contact with the peptide, the peptide is usually used in a form of a solution. Examples of methods of bringing the peptide in the form of a solution into contact with the surface of the medical device or the medical material include application, nebulization, and soaking. Among these methods, soaking is preferable. The surface of the medical device or the medical material may be made of a porous material, and the peptide can be brought into contact with the inner surface of the pores of the porous material by soaking.

The temperature and time when the peptide is brought into contact with the surface of the medical device or the medical material by soaking are not particularly limited as long as binding or attaching of the peptide to the surface of the medical device or the medical material progress satisfactorily. Soaking is performed typically at 5 to 90° C., and preferably at 20 to 70° C. Furthermore, soaking time is preferably 0.1 to 48 hours, and more preferably 1 to 24 hours.

The use amount of the peptide when the peptide is brought into contact with the surface of the medical device or the medical material is preferably 0.1 to 50 mg/m$^2$, and more preferably 5.0 to 20 mg/m$^2$ with respect to an area of the surface to be treated on the medical device or the medical material.

The concentration of the solution of the peptide to be used for the surface treatment is not particularly limited. The concentration of the solution of the peptide is typically preferably 0.01 to 10 mg/mL, and more preferably 0.02 to 5 mg/mL.

A linker compound may be caused to bind to the peptide so as to form a linker site derived from the linker compound, and then the peptide may be supported on the surface of the medical device or the medical material via the linker site. Specifically, when the surface treatment of the medical device or the medical material is performed using a linker compound, it is preferable that the surface treatment is performed by a method including performing the following (I) and (II):

(I) causing a linker site to bind to a surface of the medical device or the medical material; and (II) causing the peptide to bind to the linker site, in an arbitrary order. In other words, the above-mentioned (II) may be performed following (I), or (I) may be performed following (II).

Typical examples of the pre-treatment of the surface described above include the following treatments (1), (2), or (3).

(1) treatment such as plasma treatment, glow discharge treatment, or corona discharge treatment;

(2) chemical treatment; and (3) treatment with a linker compound.

According to the treatment (1), a hydroxyl group, a peroxide group, or a free radical or the like is generated on the pre-treated surface. Therefore, the peptide is easily adsorbed by the pre-treated surface by electrostatic affinity, hydrogen bonding, and the like. Furthermore, when a hydroxyl group is generated on the surface by pre-treatment, the peptide may be chemically fixed on the surface by esterification through reaction between the C-terminal (a carboxy group) of the peptide and a hydroxyl group. Esterification methods are not particularly limited, and examples thereof include a method using a condensing agent. Examples of the condensing agent include 2,4,6-trichlorobenzoyl chloride, 2-methyl-6-nitrobenzoic anhydride, and the like. Furthermore, esterification can also be performed using a carbodiimide compound such as N,N'-dicyclohexyl carbodiimide or 1-ethyl-3-(3-dimethylaminopropyl)carbodiimide as a condensing agent in the presence of a basic catalyst such as 4-dimethylaminopyridine.

In addition, the pre-treatment capable of generating a hydroxyl group on the surface is also useful as pre-treatment for performing pre-treatment using a linker compound. When a hydroxyl group rich in reactivity is present on the surface, the linker compound is easily caused to bind to the surface.

The treatment of (2) is a method for introducing a reactive functional group such as a hydroxyl group, a carboxy group, and an amino group on the surface of the medical device or the medical material by chemical treatment. Such treatment permits the introduction of a functional group having reactivity with respect to the peptide and a functional group that can react with a reactive group of a linker compound described later into the surface of the medical device or the medical material.

When, for example, an alkyl group or an aldehyde group is present on the surface of the medical device or the medical material, by oxidizing these groups according to ordinary methods, a carboxy group can be generated. Furthermore, when an aromatic ring is present on the surface of the medical device or the medical material, an amino group can be introduced on the surface of the medical device or the medical material by nitration by ordinary methods and reduction of a nitro group. In addition, a material such as a fluorocarbon resin can be treated with borane ($BH_3$), and then treated with an oxidizing agent such as $H_2O_2$ in the presence of a base such as NaOH, whereby a hydroxyl group can be introduced on the surface of the material. Note here that the chemical treatment method for the surface of the medical device or the medical material may be any method as long as the method can introduce a desired functional group onto the surface, and is not limited to the above-mentioned specific treatment methods.

According to the treatment of (3), the surface of the medical device or the medical material is pre-treated using a linker compound having a functional group capable of chemically binding to a peptide, and having adhesiveness to or being capable of chemically binding to the surface of the medical device or the medical material.

When the linker compound is a compound capable of chemically binding to the surface of the medical device or the medical material, the linker compound has a reactive group that reacts with a functional group present on the surface of the medical device or the medical material so as to form a covalent bond. The types of the reactive group of the linker compound can be appropriately selected corresponding to the types of functional groups present on the surface of the medical device or the medical material.

When, for example, a hydroxyl group is present on the surface of the medical device or the medical material, suitable examples of the reactive group in the linker compound include a carboxy group, an alkoxysilyl group (for example, a trimethoxysilyl group and a tritoxysilyl group), a halosilyl group (for example, a trichlorosilyl group), a halocarbonyl group (for example, a chlorocarbonyl group), an isocyanate group, an isothiocyanate group, and the like. When an amino group (—$NH_2$) is present on the surface of the medical device or the medical material, suitable examples of the reactive group in the linker compound include a carboxy group, an isocyanate group, an isothiocyanate group, an N-hydroxysuccinimide ester group (NHS ester group), a nitrophenyl ester group, a pentafluorophenyl ester group, a 1-hydroxybenzotriazole ester group (HOEt ester group), a 1-hydroxy-7-azabenzotriazole ester group (HOAt ester group), an epoxy group, and the like. When a mercapto group (—SH) is present on the surface, examples of the reactive group in the linker compound include a mercapto group, an N-substituted maleimide group, and the like.

Examples of the linker compound include a silane coupling agent having a functional group having reactivity with respect to the peptide. Suitable examples of such silane coupling agents include aminosilane coupling agents such as 3-aminopropylyltriethoxysilane and 3-aminopropyltrimethoxysilane; epoxysilane coupling agents such as 3-glycidoxypropyltriethoxysilane and 3-glycidoxypropyltrimethoxysilane; and mercaptosilane coupling agents such as 3-mercaptopropyltriethoxysilane and 3-mercaptopropyltriethoxysilane.

When the amino silane coupling agent is used, for example, by reacting the C-terminal of the peptide and an amino group with each other, the peptide can be caused to bind to the silane coupling agent serving as a linker. An epoxy group can be reacted with various functional groups such as an amino group, a carboxy group, a phenolic hydroxyl group, and the like. Therefore, when the epoxysilane coupling agent is used, as a result of the reaction of a functional group that can be reacted with an epoxy group in the peptide and the epoxy group, the peptide can be caused to bind to the silane coupling agent as a linker. A mercapto group can form a disulfide bond by the reaction of mercapto groups together. Therefore, when the mercapto silane coupling agent is used, as a result, of the reaction between a mercapto group in the peptide and a mercapto group derived from the silane coupling agent, the peptide can be caused to bind to the silane coupling agent serving as a linker.

Furthermore, other suitable examples of the linker compound include compounds having N-substituted maleimide groups such as 3-maleimidopropionic acid, 3-maleimidopropionic acid N-succinimidyl, 4-maleimidobutanoic acid, 4-maleimidobutanoic acid N-succinimidyl, 6-maleimidohexanoic acid, and 6-maleimidohexanoic acid N-succinimidyl. These compounds bind to a hydroxyl group or an amino group on the surface of the medical device or the medical material by a carboxy group or an N-hydroxysuccinimide ester group (NHS ester group), and bind to a mercapto group in the peptide by an N-substituted maleimide group.

From the viewpoint of high reactivity and ease in preferably causing a peptide to bind to the surface of the medical device or the medical material, it is preferable that a peptide including a mercapto group is used as the peptide, and that a linker site is formed using a linker compound including an N-substituted maleimide group at the terminal. In this case, the mercapto group of the peptide and the N-substituted maleimide group at the terminal of the linker site react with each other, and the peptide binds to the linker site via a sulfide bond (—S—). The method of introducing a mercapto group into the peptide is not particularly limited, but a method of introducing a cysteine residue into the peptide is preferable.

Furthermore, a peptide can be generated by binding at least two or more peptide fragments including an adhesive peptide fragment having adhesiveness with respect to the surface of the medical device or the medical material, and a peptide fragment having an amino acid sequence of any one of SEQ ID NOs: 1 to 10. In this case, the adhesive peptide fragment can be used in a similar manner to the linker compound mentioned above. The full length of the adhesive peptide fragment is not particularly limited. Preferably, the adhesive peptide fragment has a full length capable of generating a peptide with a full length within the range of the above-described suitable number of amino acid residues.

Examples of the adhesive peptide fragment include a peptide having an adhesion site made of amino acid residues including a 2,3-dihydroxyphenyl group or a 3,4-dihydroxyphenyl group. The adhesion site is as described above in the case where the adhesion site is provided in the peptide.

Furthermore, when the surface of the medical device or the medical material is made of the above-described biologically derived tissue, the adhesion site in the adhesive peptide fragment is also preferably a site having a repetitive sequence of an amino acid represented by (POG)n. The adhesion site having a repetitive sequence of an amino acid represented by (POG)n is as described above in the case where the adhesion site is provided in the peptide.

When the surface treatment of the medical device or the medical material to be used in contact with blood is performed with the method mentioned above, and the peptide including an amino acid sequence of any one of SEQ ID NOs: 1 to 10 is used in the surface treatment, a medical device or medical material capable of achieving high efficiency of endothelialization can be obtained.

Second Embodiment

A second embodiment of the present invention relates to a peptide including an amino acid sequence of any one of SEQ ID NOs: 1 to 10. The peptide is the same as the peptide described in the first embodiment.

Third Embodiment

A third embodiment of the present invention relates to a production method of a medical device or medical material being surface-treated and to be used in contact with blood, the method including causing a peptide to bind or attach to a surface of the medical device or the medical material; wherein the peptide includes an amino acid sequence of any one of SEQ ID NOs: 1 to 10.

The medical device or the medical material produced by the production method in accordance with the third embodiment is the same as the medical device or the medical material described in the first embodiment. Furthermore, the peptide to be used in the production method in accordance with the third embodiment is the same as the peptide described in the first embodiment. In addition, the binding or attaching of the peptide to the surface of the medical device or the medical material is performed as in the surface treatment method described in relation to the first embodiment.

According to the production method mentioned above, by performing the surface treatment using the peptide including an amino acid sequence of any one of SEQ ID NOs: 1 to 10, it is possible to obtain a medical device or medical material capable of achieving high efficiency of endothelialization and to be used in contact with blood.

Fourth Embodiment

A fourth embodiment of the present invention relates to a surface treatment agent for surface-treating a medical device or medical material to be used in contact with blood, wherein the surface treatment agent includes a peptide, and the peptide includes an amino acid sequence of any one of SEQ ID NOs: 1 to 10.

The medical device or the medical material as a subject to be surface-treated with the surface treatment agent in accordance with the fourth embodiment is the same as the medical device or the medical material described in the first embodiment. Furthermore, the peptide included in the surface treatment agent in accordance with the fourth embodiment is the same as the peptide described in the first embodiment.

The surface treatment agent of the fourth embodiment may be in a solid state or a liquid state, and a liquid state is preferable because a desired amount of the peptide is easily brought into uniform contact with the surface of the medical device or the medical material. In other words, the surface treatment agent is preferably a surface treatment solution. The type of the solvent included in the surface treatment solution is not particularly limited within a range where the objects of the present invention are not impaired, as long as the solvent can dissolve the peptide. Water is usually used as a solvent included in the surface treatment solution from the viewpoint of solubility of the peptide, the absence of detrimental effects on the surface of the medical device or the medical material, and the like.

The preparation method of the surface treatment solution is not particularly limited. When the peptide is in a state of a solution, a solution including the peptide is diluted or condensed such that the concentration of the peptide becomes a desired concentration so as to obtain a surface treatment solution. When a peptide is made into powder by a method such as freeze drying, peptide powder and a solvent such as water are mixed with each other at a predetermined ratio, and the peptide is dissolved in the solvent so as to obtain a surface treatment solution.

The concentration of the peptide in the surface treatment solution is not particularly limited. The preferable concentration of the peptide in the surface treatment solution is the same as that of the peptide solution described in the first embodiment.

When the surface treatment agent is a surface treatment solution, the surface treatment solution may include various additives that do not bind to a site made of the amino acid sequence of any one of SEQ ID NOs: 1 to 10 and the adhesion site in the peptide, within a range where the objects of the present invention are not impaired. Examples of the additives that can be incorporated into the surface treatment solution include pH adjusting agents, osmotic pressure regulators, surfactants, viscosity adjusting agents, stabilizers, coloring agents, perfumes, antioxidants, preservatives, antifungal agents, and ultraviolet absorbers. These additives are added to the surface treatment solution in accordance with the amount that these additives are usually incorporated into various drug solutions.

Fifth Embodiment

A fifth embodiment of the present invention relates to a set of surface treatment agents for surface-treating a medical device or medical material to be used in contact with blood, wherein the set includes a first agent including a peptide, and a second agent including a linker compound having a functional group capable of binding to a surface of the medical device or the medical material and a functional group capable of binding to the peptide, and the peptide includes an amino acid sequence of any one of SEQ ID NOs: 1 to 10.

The medical device or the medical material as a subject to be surface-treated with the set of surface treatment agents in accordance with the fifth embodiment is the same as the medical device or the medical material described in the first embodiment. Furthermore, the peptide used in the set of surface treatment agents in accordance with the fifth embodiment is the same as the peptide described in the first embodiment. In addition, the linker compound to be used in the set of surface treatment agents in accordance with the fifth embodiment is the same as the linker compound described in the first embodiment.

In the set of surface treatment agents of the fifth embodiment, the first agent and the second agent may be in a solid state or a liquid state, and a liquid state is preferable because a desired amount of the peptide or the linker compound is easily brought into uniform contact with the surface of the medical device or the medical material. In other words, the first agent and the second agent are each preferably a liquid formulation.

When the first agent including a peptide is a liquid formulation, as the liquid formulation, the same liquid as the surface treatment solution including the peptide described in the fourth embodiment can be used.

When the second agent including a linker compound is a liquid formulation, the type of solvent included in the liquid formulation is not particularly limited within a range where the objects of the present invention are not impaired as long as the solvent can dissolve the linker compound. The solvent may be water or an organic solvent or an aqueous solution of an organic solvent. Furthermore, a Good's buffer solution such as a MES (2-morpholinoethanesulfonic acid) buffer can also be used as a solvent. When the second agent is a liquid formulation, the concentration of the linker compound in the liquid formulation is not particularly limited.

When a condensation reaction occurs between the surface of the medical device or the medical material and the linker compound, or between the linker compound and the peptide, a condensing agent that promotes the condensation reaction of the set of surface treatment agents may be included.

The type of the condensing agent is not particularly limited as long as the condensing agent does not adversely affect the medical device or the medical material, and the condensing agent can be appropriately selected depending on the types of the functional groups involved in the condensation reaction. As the condensing agent, for example, the condensing agents described in relation to the first embodiment can be used.

The condensing agent may be added to the first agent, the second agent, or both the first agent and the second agent. Alternatively, the condensing agent may be used in the set of surface treatment agents as a third agent including the condensing agent. When the condensing agent is used as a third agent, the type of solvent that dissolves the condensing agent is not particularly limited as long as the solvent does not adversely affect the medical device or the medical material, and the solvent can be appropriately selected depending on the type of the condensing agent.

Sixth Embodiment

A sixth embodiment of the present invention relates to a set of surface treatment agents for surface-treating a medical device or medical material to be used in contact with blood, wherein the set includes a first agent including a peptide, and a second agent including a condensing agent for condensing a functional group present on a surface of the medical device or the medical material and a functional group of the peptide, and the peptide includes an amino acid sequence of any one of SEQ ID NOs: 1 to 10.

The medical device or the medical material as a subject to surface-treated with the set of surface treatment agents in accordance with the sixth embodiment is the same as the medical device or the medical material described in the first embodiment. Furthermore, the peptide used in the set of surface treatment agents of the sixth embodiment is the same as the peptide described in the first embodiment. In addition, the condensing agent used in the set of surface treatment agents in accordance with the sixth embodiment is the same as the condensing agent described in the first embodiment.

In the set of surface treatment agents of the sixth embodiment, the first agent and the second agent may be in a solid state or a liquid state, and a liquid state is preferable because a desired amount of the peptide or the linker compound is easily brought into uniform contact with the surface of the medical device or the medical material. In other words, the first agent and the second agent are each preferably a liquid formulation.

When the first agent including a peptide is a liquid formulation, as the liquid formulation, the same liquid as the surface treatment solution including the peptide described in the fourth embodiment can be used.

When the second agent including a condensing agent is a liquid formulation, the type of solvent included in the liquid formulation is not particularly limited within a range where the objects of the present invention are not impaired as long as the solvent can dissolve the condensing agent. The solvent may be water or an organic solvent or as aqueous solution of an organic solvent. Furthermore, a Good's buffer solution such as a MES (2-morpholinoethanesulfonic acid) buffer can also be used as a solvent. When the second agent is a liquid formulation, the concentration of the condensing agent in the liquid formulation is not particularly limited.

EXAMPLES

Hereinafter, the present invention will be described by using Examples. However, the present invention is not limited to the Examples.

Examples 1 to 10

Peptides 1 to 10 formed from amino acid sequences of SEQ ID NOs: 11 to 20 shown below were synthesized by an Fmoc solid phase synthesis method, respectively. The peptides 1 to 10 include the amino acid sequences of SEQ ID NOs: 1 to 10, respectively. The obtained peptides 1 to 10 were subjected to as immobilization reaction onto the ePTFE (expanded porous PTFE) surface.

```
                        (SEQ ID NO: 11)
GQSEKHLGGGC (SEQ ID NO: 12)
HGGVRLYGGGC (SEQ ID NO: 13)
SFKIPYHYDSGQGGGC (SEQ ID NO: 14)
SLSKWSFGGGC (SEQ ID NO: 15)
KIAVISTGGGC (SEQ ID NO: 16)
TDNTKPKGGGC (SEQ ID NO: 17)
TNWRTINGGGC (SEQ ID NO: 18)
VSRDTPQGGGC (SEQ ID NO: 19)
TIPRAPSPANTYGGGC (SEQ ID NO: 20)
NRPDSAQFWLHHGGGC
```

Firstly, an ePTFE disk (diameter: 12 mm) was washed with methanol, and then dried. The dried disk was soaked in a solution of $BH_3$ in tetrahydrofuran (THF) (1 M) for one hour. Next, the surface of the disk was reacted with $H_2O_2$/NaOH (2 g of NaOH was dissolved in 14 mL of pure water, and mixed with 30% $H_2O_2$ solution immediately before use) for one hour to introduce a hydroxyl group into the surface of the disk.

A MES (2-morpholinoethanesulfonic acid) buffer solution (pH 6, concentration of 1 mg/mL) of 6-maleimidohaxanoic acid and a MES buffer solution (pH 6, concentration of 2 mg/mL) of 1-ethyl-3-(3-dimethylaminopropyl)carbodiimide were reacted with the disk in which the hydroxyl group was introduced on the surface thereof for one hour to perform an esterification reaction of the hydroxyl groups on the surface of the disk and 6-maleimidohexanoic acid. A peptide solution in which the above-described peptides 1 to 10 were dissolved in a phosphate buffered physiological saline (PBS) at a concentration of 1.5 mg/mL, and the disk having an N-substituted maleimide group on the surface thereof were reacted with each other for one hour to bind the peptides 1 to 10 to the surface of the disk.

A reaction scheme for binding a peptide having a mercapto group (Peptide-SH) to a PTFE surface according to the above-mentioned method is shown below.

[Chem. 1]

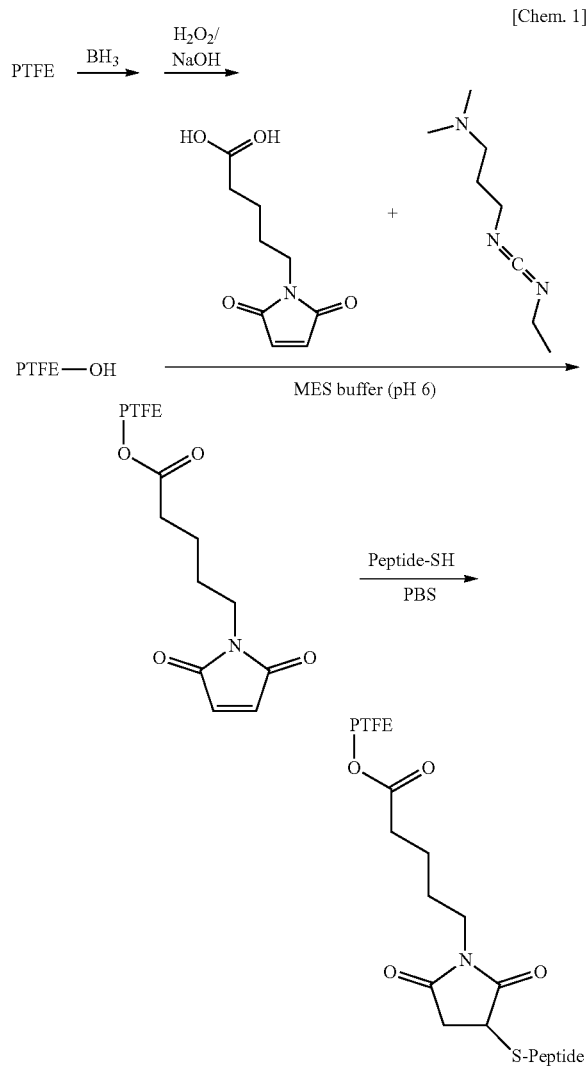

Comparative Examples 1 and 2

A surface-unmodified ePTFE disk was used as a disk in Comparative Example 1. Furthermore, an ePTFE disk in which a hydroxyl group had been introduced in the surface thereof according to the method of Examples 1 to 10 was used as a disk in Comparative Example 2.

<Evaluation of Cellular Adhesiveness>

To the disks whose surface was surface-modified with the peptides 1 to 10 in accordance with Examples 1 to 10, to the surface-unmodified disk in accordance with Comparative Example 1, and to the disk in which a hydroxyl group was introduced on the surface thereof in accordance with Comparative Example 2, $2 \times 10^4$ human umbilical vein endothelial cells (HUVEC) were seeded, respectively, cultured for 4 hours or 48 hours, and then the numbers of cultured cells were counted using Cell Counting Kit-8. Specifically, the disks modified with peptides were placed in wells of a 24-well plate, and fixed to the bottom surface with a stainless steel ring for testing. The HUVEC cells were purchased from BioChain Institute Inc. Culture was performed in a medium in which EGM-2 additive agent (Catalogue #CC4176, Lonza) had been added into a vascular endothelial cell basal medium (EBM-2) (Clonetics, San Diego, Calif.) in an environment at 37° C. and at 5% $CO_2$ for 4 hours and 48 hours. Counting of the number of cells was performed after non-adhesion cells had been removed. The results of counting the cells are shown in Table 1.

Furthermore, for Examples 2, 4, 5, and 10, and Comparative Examples 1 and 2, the forms of the cells on the disk surface after 4 hours were observed under an SEM (scanning electron microscope) and a confocal microscope. As a result, in Examples 2, 4, 5, and 10, excellent extension of cells was confirmed, and extension of philipodia was observed. On the other hand, in Comparative Examples 1 and 2, no significant increase in cell proliferation was observed.

In addition, for Examples 2 and 5, and Comparative Examples 1 and 2, the forms of the cells on the disk surface after 48 hours were observed under an SEM (scanning electron microscope) and a confocal microscope. As a result, in Examples 2 and 5, significant cell proliferation and extension of philipodia were observed. On the other hand, in Comparative Examples 1 and 2, no significant increase in cell proliferation was observed.

TABLE 1

| | Peptide | | Number of cells | |
| --- | --- | --- | --- | --- |
| | Type | SEQ ID NO | After 4 hours | After 48 hours |
| Example 1 | Peptide 1 | 11 | 13510 ± 1080 | 19539 ± 5650 |
| Example 2 | Peptide 2 | 12 | 18623 ± 2886 | 27105 ± 4157 |
| Example 3 | Peptide 3 | 13 | 11087 ± 2704 | 23852 ± 5875 |
| Example 4 | Peptide 4 | 14 | 18192 ± 488 | 21002 ± 3506 |
| Example 5 | Peptide 5 | 15 | 15801 ± 1274 | 23115 ± 3773 |
| Example 6 | Peptide 6 | 16 | 4108 ± 2316 | 12660 ± 2142 |
| Example 7 | Peptide 7 | 17 | 11283 ± 3189 | 22481 ± 5753 |
| Example 8 | Peptide 8 | 18 | 9427 ± 2914 | 22059 ± 6769 |
| Example 9 | Peptide 9 | 19 | 10750 ± 1793 | 21125 ± 6201 |
| Example 10 | Peptide 10 | 20 | 13816 ± 4497 | 15943 ± 2936 |
| Comparative example 1 | Untreated disk | | 9655 ± 1623 | 6246 ± 3965 |
| Comparative example 2 | Hydroxy group-introduced test piece | | 1395 ± 2114 | 11444 ± 43322 |

According to the results shown in Table 1, it is recognized that surface treatment using peptides 1 to 10 having the amino acid sequences of SEQ ID NOs: 11 to 20, including the amino acid sequences of SEQ ID NOs: 1 to 10 respectively, have an action for promoting the adhesion of human umbilical vein endothelial cells (HUVEC).

Examples 11 to 20

Treatment of binding a peptide to the surface of an ePTFE suture (Gore-Tex (registered trademark) fiber) was performed by using each peptide described in Table 2 (peptides 1 to 10), in the same manner as in Examples 1 to 10.

Comparative Example 3

A surface-unmodified ePTFE suture was used as a suture in Comparative Example 3.
<Whole Blood Contact Test In Vivo>
The ePTFE sutures of Examples 11 to 20 and Comparative Example 3 were disposed such that they were oriented in parallel to the blood flow direction in the vicinity of a tube inner wall of a tube-type connector having an inner diameter of 10 mm and a full length of 65 mm. Next, the ePTFE suture was fixed in the connector by fitting two polypropylene tubes each having an inner diameter of 6 mm and an outer diameter of 10 mm into both ends of the connector to a depth of 5 mm. A tube-type cartridge including the thus prepared ePTFE suture therewithin was sterilized with ethylene oxide gas, and then subjected to a test in vivo.

As an animal for testing, a miniature pig (Göttingen, male, 25 to 30 kg) was used. An artificial heart-lung circuit was constructed using the miniature pig by inserting a blood delivery cannula into the ascending aorta and a blood removal cannula through the right atrial appendage. To the artificial heart-lung circuit, blood removal cannula/cartridge for testing/venous blood reservoir/blood transport pump/artificial lung/blood delivery cannula were linked in this order. Using the artificial heart-lung circuit having the above-mentioned configuration, blood to which heparin had been administered was caused to flow for one hour such that the activated whole blood clotting time (ACT) became 400 or more.
<Check of Cell Adhesion>
For the ePTFE sutures of Examples 11, 12, and 20, cell adhesion was checked according to the following method. After blood was caused to flow for one hour, the cartridges were collected, and the ePTFE sutures in the cartridges were washed with a physiological saline solution. Next, using 4% glutaraldehyde, the ePTFE sutures were subjected to immobilization treatment.

Next, surface markers of the cells adhering to the ePTFE sutures of Examples 11, 12, and 20 were evaluated by fluorescence immunostaining. The nucleus was stained with a PBS solution (10 μg/mL) of DAPI (4′,6-diamidino-2-phenylindole). The antibodies used for fluorescence immunostaining were CD34, CD105, and Flk-1 antibodies labelled with PE (phycoerythrin). A vascular endothelial progenitor cell expresses CD34, CD105, and Flk-1 antibodies. After the immobilization treatment of the ePTFE sutures of Examples 11, 12, and 20, a 100-fold diluted antibody solution was added thereto and incubated for 1 hour at room temperature, and then the cells on the surface of the ePTFE suture were observed by confocal laser microscopy. As a result, in all the ePTFE sutures of Examples 11, 12, and 20, cells stained with CD34, CD105, and Flk-1 antibodies were observed. In other words, the cells adhering to the surface of the ePTFE sutures of Examples 11, 12, and 20 were considered to be vascular endothelial progenitor cells.
<Platelet Stickiness Evaluation>
The ePTFE sutures of Examples 11 to 20, and Comparative Example 3 were evaluated according to the following method in terms of a platelet sticking area and a water contact angle. These evaluation results are shown in Table 2.
(Measurement of Platelet Sticking Area)
Platelet rich plasma was formed using citrated blood collected from a miniature pig in the following manner. Firstly, the collected blood was centrifuged at 600 G for 4 minutes, and then a supernatant was collected and the number of platelets in the supernatant was counted using a Z2 Coulter Counter. Furthermore, the collected blood was centrifuged at 1300 G for 120 minutes to form a platelet poor plasma. Both were used to prepare platelet rich plasma at $2\times10^7$ platelets/mL. Each sample was brought into contact with the platelet suspension at 37° C. for one hour, washed with PBS three times, treated with a PBS solution of formaldehyde (3.7 v/v) for 10 minutes for immobilization. Then, after treatment with Triton X-100 (0.1 v/v %) for three minutes, staining treatment with a Rhodamine-Phalloidin stain solution was performed for 30 minutes. After washing, washing with PBS was performed three times, the surface of the sample was photographed using a fluorescence microscope (Olympus IX80 (Olympus Hamburg, Germany)), and the percentage of the area covered with platelets in the sample was measured using Image J software.
(Measurement of Water Contact Angle)
A static contact angle was measured by a droplet method using a contact angle measurement apparatus CA-X (Kyowa Interface Science Co., Ltd.). One minute after dropping pure water, a droplet image was photographed and a contact angle was measured.

TABLE 2

| | Peptide | | Platelet | Water contact |
|---|---|---|---|---|
| | Type | SEQ ID NO | sticking area (Area percentage) | angle (°) |
| Example 11 | Peptide 1 | 11 | 47.9% ± 16.9 | 118 ± 3.5 |
| Example 12 | Peptide 2 | 12 | 1.8% ± 1.5 | 21.8 ± 7 |
| Example 13 | Peptide 3 | 13 | 40.1% ± 22.1 | 107.2 ± 22.5 |
| Example 14 | Peptide 4 | 14 | 20.5% ± 17.3 | 45.6 ± 2.3 |
| Example 15 | Peptide 5 | 15 | 3.7% ± 2.7 | 40.9 ± 16 |
| Example 16 | Peptide 6 | 16 | 33.5% ± 13.8 | 120.9 ± 4.5 |
| Example 17 | Peptide 7 | 17 | 36.2% ± 8 | 107.7 ± 6.5 |
| Example 18 | Peptide 8 | 18 | 58.4% ± 13.4 | 120 ± 2.9 |
| Example 19 | Peptide 9 | 19 | 34.9% ± 23.3 | 122.8 ± 2.9 |
| Example 20 | Peptide 10 | 20 | 24.9% ± 16.3 | 11.2 ± 3.7 |
| Comparative example 3 | Untreated suture | | 65.5% ± 7.9 | 133.6 ± 3.7 |

According to the results shown in Table 2, it is recognized that surface treatment using peptides 1 to 10 having the amino acid sequences of SEQ ID NOs: 11 to 20, including the amino acid sequences of SEQ ID NOs: 1 to 10 respectively, have an action of suppressing the sticking of the platelets.

Examples 21 to 30

Treatment of causing a peptide to bind to a surface of an ePTFE disk (diameter: 12 mm) was performed by using each peptide described in Table 3 (peptides 1 to 10), in the same manner as in Examples 1 to 10.

Comparative Examples 4 and 5

A surface-unmodified ePTFE disk was used as a test piece in Comparative Example 4. Furthermore, an ePTFE disk in which a hydroxyl group had been introduced in the surface by the same manner as in Examples 1 to 10 was used as a test piece in Comparative Example 5.
<Evaluation of Adhesiveness of EPC (Human Vascular Endothelial Progenitor Cells)>
Using the test pieces of ePTFE surface-treated with peptides in Examples 21 to 30 and test pieces which were not surface-treated with peptides in Comparative Examples 4 and 5, evaluation of adhesiveness of EPC (human vascular endothelial progenitor cells) was performed by the same method as in the evaluation of cellular adhesiveness in Examples 1 to 10 and Comparative Examples 1 and 2, except that EPC was seeded at a density of $1.5\times10^4$ (cells/well) instead of seeding human umbilical vein endothelial cells (HUVEC) at a density of $2\times10^4$ (cells/well), and culture time was changed from 4 hours and 48 hours to only 4 hours.

TABLE 3

| | Peptide | | Number of cells |
|---|---|---|---|
| | Type | SEQ ID NO | After 4 hours |
| Example 21 | Peptide 1 | 11 | 3894 ± 2611 |
| Example 22 | Peptide 2 | 12 | 7548 ± 589 |
| Example 23 | Peptide 3 | 13 | 4680 ± 1841 |
| Example 24 | Peptide 4 | 14 | 5262 ± 1561 |
| Example 25 | Peptide 5 | 15 | 4606 ± 2471 |
| Example 26 | Peptide 6 | 16 | 3815 ± 857 |
| Example 27 | Peptide 7 | 17 | 5339 ± 1656 |

TABLE 3-continued

| | Peptide | | Number of cells |
|---|---|---|---|
| | Type | SEQ ID NO | After 4 hours |
| Example 28 | Peptide 8 | 18 | 8322 ± 2758 |
| Example 29 | Peptide 9 | 19 | 5328 ± 1972 |
| Exarrple 30 | Peptide 10 | 20 | 5252 ± 591 |
| Comparative example 4 | Untreated test piece | | 2989 ± 1368 |
| Comparative example 5 | Hydroxy group-introduced test piece | | 2328 ± 1349 |

According to the results of Table 3, it is recognized that surface treatment using peptides 1 to 10 having the amino acid sequences of SEQ ID NOs: 11 to 20, including the amino acid sequences of SEQ ID NOs: 1 to 10 respectively, have an action of promoting adhesion of EPC (human vascular endothelial progenitor cells) even in a short-time culture of about four hours.

The invention claimed is:

1. A production method of a medical device or medical material being surface-treated and to be used in contact with blood, the method comprising:
   binding or attaching a peptide comprising an amino acid sequence of SEQ ID NO: 2 to a surface of the medical device or the medical material,
   wherein the peptide is attached or bound to the surface of the medical device or the medical material by:
   (i) plasma treatment, glow discharge treatment, or corona discharge treatment;
   (ii) an esterification reaction between a surface of the medical device or medical material on which a hydroxy group is introduced by plasma treatment, glow discharge treatment, or corona discharge treatment, and the C-terminus of the peptide;
   (iii) a reaction between a hydroxy group, a carboxy group, or an amino group introduced by chemical treatment to a surface of the medical device or medical material and the peptide;
   (iv) a linker compound having a carboxy group, an alkoxysilyl group, a halosilyl group, a halocarbonyl group, an isocyanate group, or an isothiocyanate group as a functional group that reacts with a hydroxy group on the surface of the medical device or medical material, and an amino group, an epoxy group, or a mercapto group as a functional group that reacts with the peptide;
   (v) a linker compound having a carboxy group, an isocyanate group, an isothiocyanate group, an N-hydroxysuccinimide ester group, a nitrophenyl ester group, a pentafluorophenyl ester group, a 1-hydroxybenzotriazole ester group, a 1-hydroxy-7-azabenzotriazole ester group, or an epoxy group as a functional group that reacts with an amino group on the surface of the medical device or medical material, and an amino group, an epoxy group, or a mercapto group as a functional group that reacts with the peptide;
   (vi) a linker compound having a mercapto group or a N-substituted maleimide group as a functional group that reacts with a mercapto group on the surface of the medical device or medical material, and an amino group, an epoxy group, or a mercapto group as a functional group that reacts with the peptide;

(vii) a linker compound having an N-substituted maleimide group, and a carboxy group or an N-hydroxysuccinimide ester group, whereby the linker compound binds the peptide via a reaction between the N-substituted maleimide group and a mercapto group included in the peptide, and whereby the linker binds to a surface of the medical device or medical material via a reaction between the carboxy group or the N-hydroxysuccinimide ester group and a hydroxy group or an amino group on the surface of the medical device or medical material;

(viii) a peptide fragment having an adhesion site made of amino acid residues including a 2,3-dihydroxyphenyl group or a 3,4-dihydroxyphenyl group as a linker compound; or (ix) a peptide fragment having an adhesion site made of peptide comprising a repetitive sequence of amino acids represented by (POG)n as a linker compound, wherein P represents proline, O represents hydroxyproline, G represents glycine, and n represents the number of repetitions of the amino acid sequence in the parentheses; and wherein the method comprises performing the following (I) and (II):

(I) binding a linker to a surface of the medical device or the medical material; and (II) binding the peptide comprising an amino acid sequence of SEQ ID NO: 2 to the linker, wherein (II) is performed following (I), or (I) is performed following (II).

2. The production method according to claim 1, wherein the peptide comprising an amino acid sequence of SEQ ID NO: 2 is attached or bound to the surface of the medical device by a linker compound having an N-substituted maleimide group, and a carboxy group or an N-hydroxysuccinimide ester group, whereby the linker compound binds the peptide via a reaction between the N-substituted maleimide group and a mercapto group included in the peptide, and whereby the linker binds to a surface of the medical device or medical material via a reaction between the carboxy group or the N-hydroxysuccinimide ester group and a hydroxy group or an amino group on the surface of the medical device or medical material.

3. A production method of a medical device or medical material being surface-treated and to be used in contact with blood, the method comprising:

binding or attaching a peptide comprising an amino acid sequence of SEQ ID NO: 2 to a surface of the medical device or the medical material, wherein the peptide is attached or bound to the surface of the medical device or the medical material by:

(i) plasma treatment, glow discharge treatment, or corona discharge treatment;

(ii) an esterification reaction between a surface of the medical device or medical material on which a hydroxy group is introduced by plasma treatment, glow discharge treatment, or corona discharge treatment, and the C-terminus of the peptide;

(iii) a reaction between a hydroxy group, a carboxy group, or an amino group introduced by chemical treatment to a surface of the medical device or medical material and the peptide;

(iv) a linker compound having a carboxy group, an alkoxysilyl group, a halosilyl group, a halocarbonyl group, an isocyanate group, or an isothiocyanate group as a functional group that reacts with a hydroxy group on the surface of the medical device or medical material, and an amino group, an epoxy group, or a mercapto group as a functional group that reacts with the peptide;

(v) a linker compound having a carboxy group, an isocyanate group, an isothiocyanate group, an N-hydroxysuccinimide ester group, a nitrophenyl ester group, a pentafluorophenyl ester group, a 1-hydroxybenzotriazole ester group, a 1-hydroxy-7-azabenzotriazole ester group, or an epoxy group as a functional group that reacts with an amino group on the surface of the medical device or medical material, and an amino group, an epoxy group, or a mercapto group as a functional group that reacts with the peptide;

(vi) a linker compound having a mercapto group or a N-substituted maleimide group as a functional group that reacts with a mercapto group on the surface of the medical device or medical material, and an amino group, an epoxy group, or a mercapto group as a functional group that reacts with the peptide;

(vii) a linker compound having an N-substituted maleimide group, and a carboxy group or an N-hydroxysuccinimide ester group, whereby the linker compound binds the peptide via a reaction between the N-substituted maleimide group and a mercapto group included in the peptide, and whereby the linker binds to a surface of the medical device or medical material via a reaction between the carboxy group or the N-hydroxysuccinimide ester group and a hydroxy group or an amino group on the surface of the medical device or medical material;

(viii) a peptide fragment having an adhesion site made of amino acid residues including a 2,3-dihydroxyphenyl group or a 3,4-dihydroxyphenyl group as a linker compound; or (ix) a peptide fragment having an adhesion site made of peptide comprising a repetitive sequence of amino acids represented by (POG)n as a linker compound, wherein P represents proline, O represents hydroxyproline, G represents glycine, and n represents the number of repetitions of the amino acid sequence in the parentheses; and wherein the medical device comprises one or more selected from the group consisting of an artificial blood vessel, a stent, an artificial valve, a catheter, a balloon, an artificial heart pump, and an artificial lung.

4. A production method of a medical device or medical material being surface-treated and to be used in contact with blood, the method comprising:

binding or attaching a peptide comprising an amino acid sequence of SEQ ID NO: 2 to a surface of the medical device or the medical material, wherein the peptide is attached or bound to the surface of the medical device or the medical material by:

(i) plasma treatment, glow discharge treatment, or corona discharge treatment;

(ii) an esterification reaction between a surface of the medical device or medical material on which a hydroxy group is introduced by plasma treatment, glow discharge treatment, or corona discharge treatment, and the C-terminus of the peptide;

(iii) a reaction between a hydroxy group, a carboxy group, or an amino group introduced by chemical treatment to a surface of the medical device or medical material and the peptide;

(iv) a linker compound having a carboxy group, an alkoxysilyl group, a halosilyl group, a halocarbonyl group, an isocyanate group, or an isothiocyanate group as a functional group that reacts with a hydroxy group on the surface of the medical device or medical material, and an amino group, an epoxy group, or a mercapto group as a functional group that reacts with the peptide;

(v) a linker compound having a carboxy group, an isocyanate group, an isothiocyanate group, an N-hydroxysuccinimide ester group, a nitrophenyl ester group, a pentafluorophenyl ester group, a 1-hydroxybenzotriazole ester group, a 1-hydroxy-7-azabenzotriazole ester group, or an epoxy group as a functional group that reacts with an amino group on the surface of the medical device or medical material, and an amino group, an epoxy group, or a mercapto group as a functional group that reacts with the peptide;

(vi) a linker compound having a mercapto group or a N-substituted maleimide group as a functional group that reacts with a mercapto group on the surface of the medical device or medical material, and an amino group, an epoxy group, or a mercapto group as a functional group that reacts with the peptide;

(vii) a linker compound having an N-substituted maleimide group, and a carboxy group or an N-hydroxysuccinimide ester group, whereby the linker compound binds the peptide via a reaction between the N-substituted maleimide group and a mercapto group included in the peptide, and whereby the linker binds to a surface of the medical device or medical material via a reaction between the carboxy group or the N-hydroxysuccinimide ester group and a hydroxy group or an amino group on the surface of the medical device or medical material;

(viii) a peptide fragment having an adhesion site made of amino acid residues including a 2,3-dihydroxyphenyl group or a 3,4-dihydroxyphenyl group as a linker compound; or (ix) a peptide fragment having an adhesion site made of peptide comprising a repetitive sequence of amino acids represented by (POG)n as a linker compound, wherein P represents proline, O represents hydroxyproline, G represents glycine, and n represents the number of repetitions of the amino acid sequence in the parentheses; and wherein the medical material comprises one selected from the group consisting of a fiber, a film, a sheet, a bag, a tube, a woven fabric, a nonwoven fabric, a molded product, and a biologically derived tissue, as well as a composite material including two or more of these materials.

* * * * *